United States Patent [19]

Steffee

[11] Patent Number: 4,696,290
[45] Date of Patent: Sep. 29, 1987

[54] APPARATUS FOR STRAIGHTENING SPINAL COLUMNS

[75] Inventor: Arthur D. Steffee, Moreland Hills, Ohio

[73] Assignee: AcroMed Corporation, Cleveland, Ohio

[21] Appl. No.: 846,018

[22] Filed: Mar. 31, 1986

Related U.S. Application Data

[62] Division of Ser. No. 562,438, Dec. 16, 1983, Pat. No. 4,611,581.

[51] Int. Cl.⁴ .............................................. A61F 5/04
[52] U.S. Cl. .................... 128/69; 128/92 YP; 128/92 YM
[58] Field of Search ........ 128/92 YP, 92 YM, 92 YF, 128/92 YE, 69

[56] References Cited

U.S. PATENT DOCUMENTS

| | | | |
|---|---|---|---|
| 3,244,170 | 4/1966 | McElvenny | 128/92 YP |
| 3,596,656 | 8/1971 | Kaute | 128/92 YF |
| 3,648,691 | 3/1972 | Lumb et al. | 128/92 YM |
| 4,524,765 | 6/1985 | de Zbikowski | 128/92 YP |
| 4,611,581 | 9/1986 | Steffee | 128/92 YF |

Primary Examiner—C. Fred Rosenbaum
Assistant Examiner—C. W. Shedd
Attorney, Agent, or Firm—Tarolli, Sundheim & Covell

[57] ABSTRACT

An improved apparatus is provided to reduce the extent of displacement between adjacent vertebrae in a person's spinal column and to subsequently maintain the vertebrae in a reduced displacement relationship. When the apparatus is to be installed, holes are formed in the displaced vertebra and in vertebrae on opposite sides of the displaced vertebra. Force transmitting members are mounted in the holes in the vertebrae. A spinal plate is then positioned on the spinal column with the force transmitting members extending outwardly through slots in the spinal plate. Nuts are tightened on the force transmitting members connected with vertebrae on opposite sides of the displaced vertebra to anchor the spinal plate in place. A nut on the force transmitting member connected with the displaced vertebra is then tightened to pull the displaced vertebra to a desired position. In one embodiment of the invention, the force transmitting member has a relatively large diameter helix which engages a side wall of the hole in the displaced vertebra. In another embodiment of the invention, an insert is positioned in a hole in the displaced vertebra and expanded by the force transmitting member to securely grip the vertebra.

8 Claims, 14 Drawing Figures

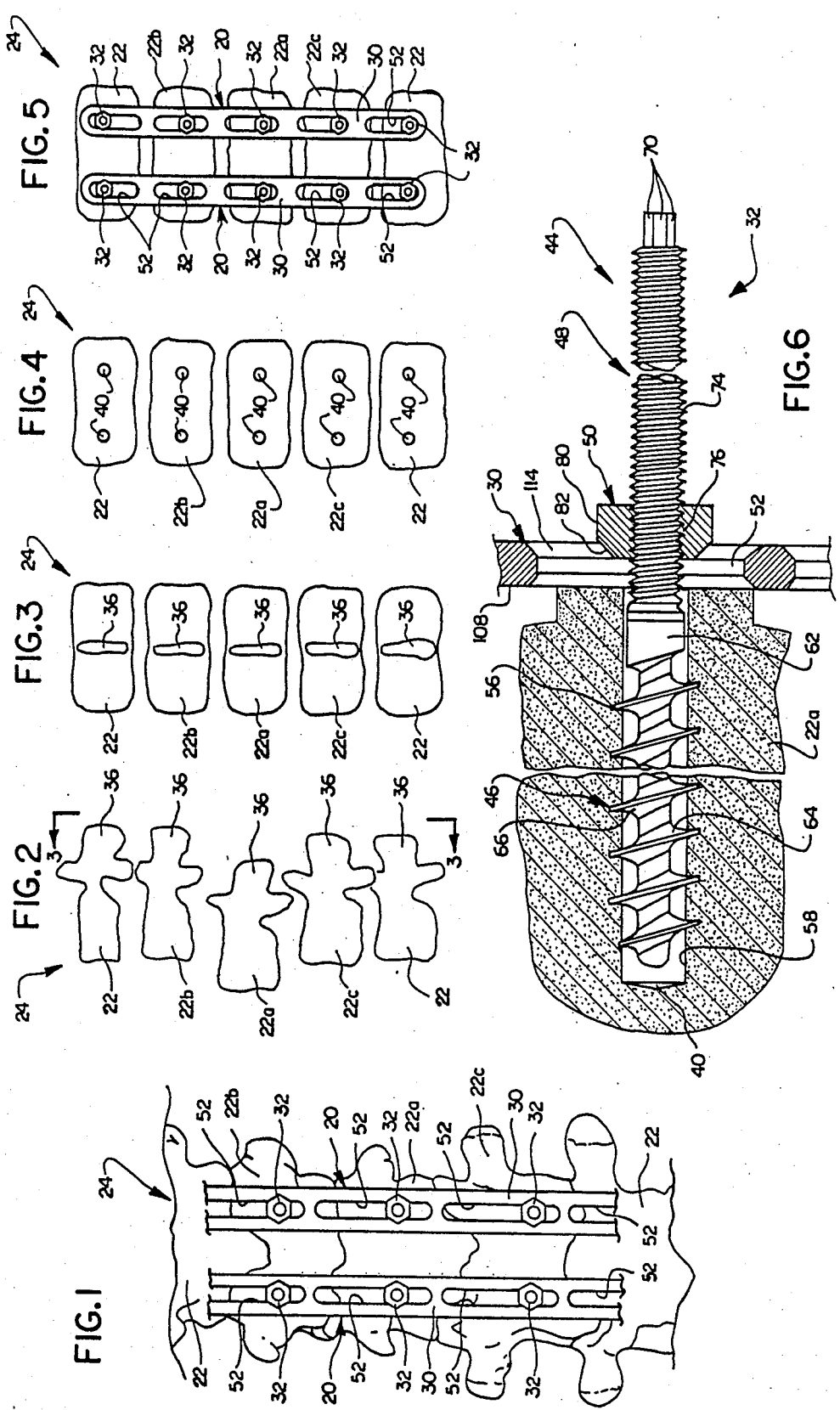

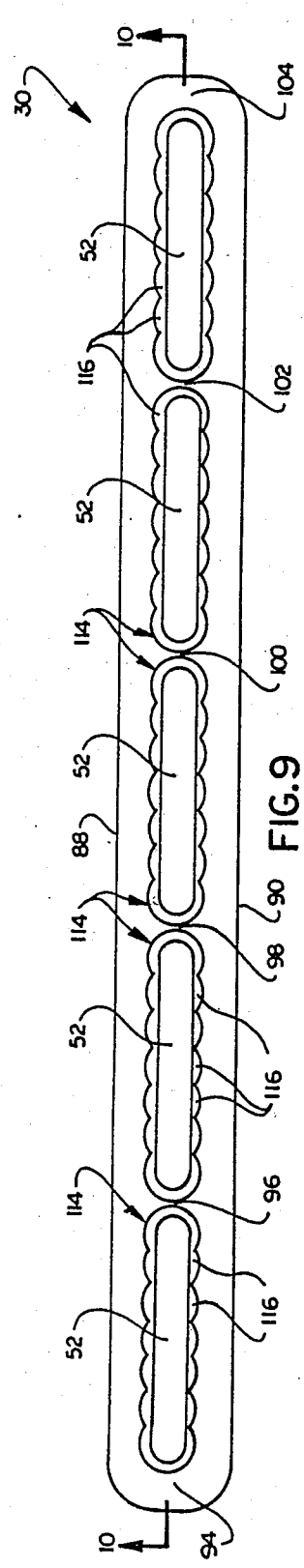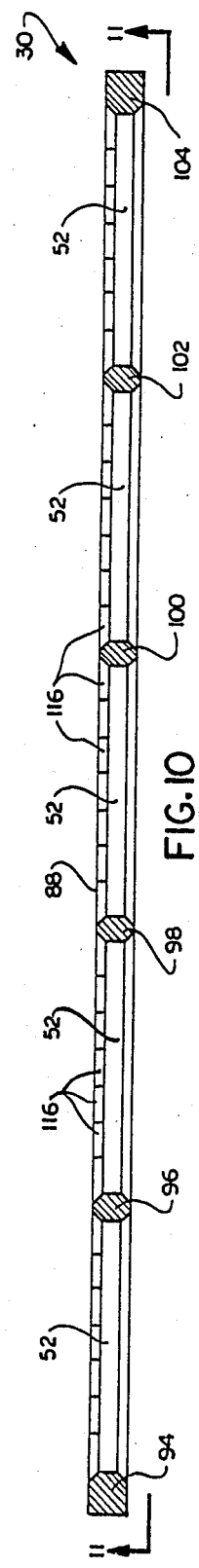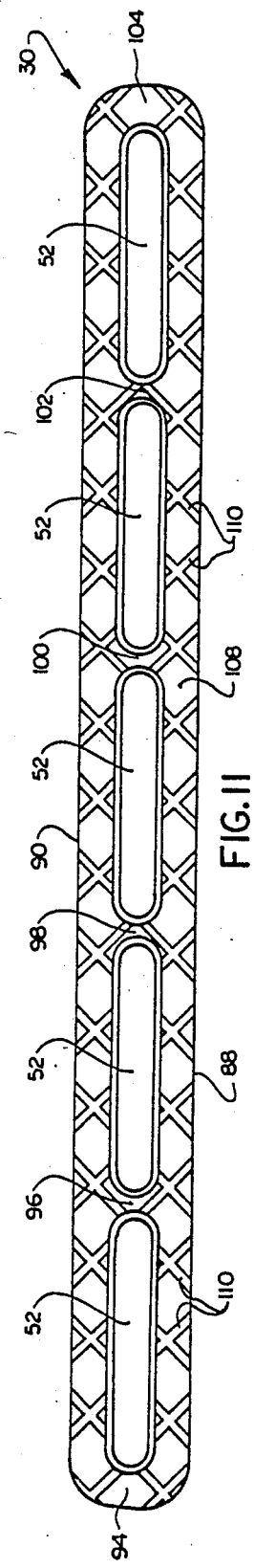

APPARATUS FOR STRAIGHTENING SPINAL COLUMNS

This is a division of application Ser. No. 562,438, filed Dec. 16, 1983, now U.S. Pat. No. 4,611,581.

BACKGROUND OF THE INVENTION

The present invention relates to a new and improved apparatus for straightening a spinal column of a human by reducing the extent of displacement between adjacent vertebrae and maintaining the vertebrae in a reduced displacement relationship.

An apparatus for use in spinal fixation is disclosed in British Pat. No. 780,652. The apparatus disclosed in this patent includes a pair of rigid plates which engage opposite sides of spinous processes projecting from vertebrae. Bolts extend through slots formed in the rigid plates and through holes formed in the spinous processes. The bolts are rotated relative to stationary nuts to press the plates against opposite sides of the spinous processes.

An article entitled "Rhamatisme Vertebra" by Roy-Camille, Sailliant and Judet discloses the use of a rigid plate to hold vertebrae in a desired relationship with each other. When the plate is to be mounted on a spinal column, accurately located holes are drilled in the vertebrae. Holes in the plate are then positioned in alignment with the vertebrae holes. Screws are then twisted into the vertebrae to clamp the plate and vertebrae together.

SUMMARY OF THE PRESENT INVENTION

The present invention provides an apparatus which reduces the extent of displacement between adjacent vertebrae by pulling a displaced vertebra into a desired position and maintaining it in the desired position. When the apparatus is to be installed on a person's spinal column, one force transmitting member is mounted in an opening formed in the displaced vertebra and at least one other force transmitting member is mounted in an opening in an adjacent vertebra. The force transmitting member preferably have a portion which securely locks in part of the bone of the vertebra in which they are mounted and a threaded portion which projects outwardly from the vertebrae. A spinal plate is then positioned so that it extends across the displaced vertebra into abutting engagement with vertebrae on opposite sides of the displaced vertebra.

The spinal plate has a series of openings therein for receiving the threaded portions of the force transmitting members. The openings are elongated slots so that the positioning of the spinal plate and the force transmitting members can vary. This allows the force transmitting members to be positioned on the vertebra where desired and enables the spine plate to be used with different size vertebra and vertebra which are spaced differently.

After the spine plate is located with force transmitting members extending through the slots thereof, the displaced vertebra is pulled into the desired relationship with adjacent vertebrae by tightening a nut on an outwardly projecting end portion of the force transmitting member. Since the force transmitting member was previously connected with the displaced vertebra, tightening of the nut applies little or no torsional force to the displaced vertebra. Therefore, tightening the nut pulls the displaced vertebra straight outward toward the desired position with a minimum of twisting of the displaced vertebra. Also, nuts are threaded onto the threaded portion of the force transmitting member or members in the vertebrae adjacent to the displaced vertebra. As a result, the vertebrae are secured together in a straightened condition by the spine plate.

The spine plate has a series of conical recesses in which the nuts which are also conical rest. The series of recesses are located along the slots through which the threaded portion of the force transmitting member extends. Thus, the ability to locate the force transmitting members as desired in the vertebrae is maintained.

BRIEF DESCRIPTION OF THE DRAWINGS

The foregoing and other objects and features of the present invention will become more apparent upon a consideration of the following description taken in connection with the accompanying drawings wherein:

FIG. 1 is a fragmentary dorsal view of a portion of a vertebral or spinal column on which apparatus constructed in accordance with the present invention has been installed to reduce the extent of displacement between adjacent vertebrae;

FIG. 2 is a schematic illustration of the vertebral column of FIG. 1 prior to movement of a displaced vertebrae to a desired position relative to adjacent vertebrae by the apparatus illustrated in FIG. 1;

FIG. 3 is a view, taken generally along the line 3—3 of FIG. 2, further illustrating the vertebral column;

FIG. 4 is a view, generally similar to FIG. 3, of the vertebral column with spinous processes removed from the vertebrae and with holes formed in the vertebrae;

FIG. 5 is a view illustrating the manner in which spinal plates are mounted on the vertebrae of FIG. 4 to move a displaced vertebra into a desired position relative to adjacent vertebrae;

FIG. 6 is an enlarged fragmentary illustration depicting the manner in which one end portion of a force transmitting member engages a vertebra and the opposite end portion of the force transmitting member engages a nut which presses against a spinal plate;

FIG. 9 is a top plan view of the spinal plate;

FIG. 10 is a sectional view of the spinal plate taken along the line 10—10 of FIG. 9;

FIG. 11 is a bottom plan view of the spinal plate, taken generally along the line 11—11 of FIG. 10;

DESCRIPTION OF SPECIFIC PREFERRED EMBODIMENTS OF THE INVENTION

General Description

Figure 7:
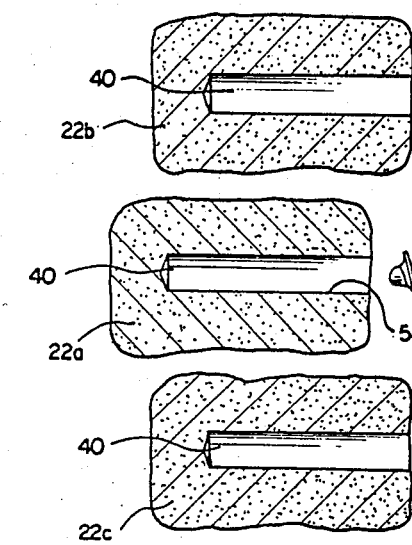
FIG. 7 is an enlarged schematic illustration depicting the manner in which the force transmitting member of FIG. 6 is mounted in a hole formed in a displaced vertebra.

A pair of assemblies 20 for reducing the extent of displacement between adjacent vertebrae 22 and maintaining the vertebrae in the reduced displacement relationship are illustrated in FIG. 1 installed on a person's vertebral or spinal column 24. Each of the assemblies 20 includes an elongated rigid spinal plate 30 which is mounted on the vertebrae 22 by a plurality of identical fastener assemblies 32.

The illustrated spinal plates 30 have a length so as to span five adjacent vertebrae 22 (see FIG. 5). A pair of fastener assemblies 32 is provided for each vertebra 22 to connect it with each of the spinal plate 30.

Prior to installation of the assemblies 20, a vertebra 22a occupies a displaced position relative to adjacent vetebrae 22b and 22c (see FIGS. 2 and 3). The assemblies 20 are installed to reduce the extent of displacement between the vertebra 22a and the adjacent vertebrae 22b and 22c. Once installed, the assemblies 20 maintain the vertebra 22a in the reduced displacement relationship with the adjacent vertebrae 22b and 22c.

When the assemblies 20 are to be installed, the sharp blunt spinous processes 36 which project from the vertebrae 22 (FIGS. 2 and 3) are removed (FIG. 4). A pair or series of vertically aligned holes 40 (see FIG. 4) are then drilled in the vertebrae 22. The fastener assemblies 32 are mounted in the holes 40.

The fastener assemblies 32 associated with the vertebrae 22 which are above and below the displaced vertebra 22a are tightened to anchor the spinal plates 30 in place bridging the space across the displaced vertebra 22a. The fastener assemblies 32 connected with the displaced vertebrae 22a are then tightened to pull the displaced vertebrae 22a toward the right (as viewed in FIG. 2). This reduces the extent of displacement between the vertebra 22a and the adjacent vertebrae 22. The fastener assemblies 32 cooperate with the vertebrae 22 and the spinal plates 30 to maintain the displaced vertebra 22a in the reduced displacement position relative to the adjacent vertebrae.

Fastener Assembly—First Embodiment

Each of the identical fastener assemblies 32 includes an axially extending stainless steel force transmitting member 44 (FIG. 6). The force transmitting member 44 has a mounting end portion 46 which is received in a cylindrical hole 40 in a vertebra 22 and a retaining end portion 48 which engages a nut 50. The force transmitting member 44 extends through an elongated slot 52 formed in the spinal plate 30. Therefore, when the nut 50 is tightened, the spinal plate 30 is pressed against the vertebra 22.

The mounting end portion 46 of the force transmitting member 44 is provided with a relatively large diameter helix 56 (FIGS. 6 and 7). When the force transmitting member 44 is pressed axially into a hole 40 in a vertebra and rotated, the helix 56 screws itself into the hole. The helix 56 has a substantially larger crest diameter than the inside diameter of the hole 40 so that the helix cuts into the cylindrical side surface 58 of the hole 40 to firmly mount the force transmitting member 44 in the vertebra 22.

The force transmitting member 50 has a very short cylindrical shank portion 62 (FIG. 6) with an outside diameter corresponding to the outside diameter of a cylindrical stainless blank from which the force transmitting member 44 was formed. In order to provide a solid grip between the helix 56 and vertebra 22, the metal of the blank was worked to form the helix 56 with a relatively large crest diameter and a relatively small root diameter. This results in the helix having flank surfaces 64 and 66 which project into the bone of the vertebra 22 for a substantial distance to firmly hold the force transmitting member 44 against axial movement relative to the vertebra 22.

The helix 56 is turned into the hole 40, which has a diameter which is only slightly greater than the diameter of the shank 62, by applying torque to wrenching flats 70 formed on the retaining end portion 48 of the force transmitting member 44. If desired, a slot or other aperture could be formed to receive a screwdriver rather than having wrenching flats 70.

The retaining end portion 48 of the force transmitting member 40 has a standard external screw thread 74 (FIG. 6) which engages a standard internal thread 76 formed in the nut 50. The nut 50 has wrenching flats 80 which are gripped by a suitable wrench to rotate the nut relative to the external thread 74. A conical leading end portion 82 of the nut 50 moves into abutting engagement with the spinal plate 30 as the nut is tightened onto the force transmitting member 44.

Installation

When the assemblies 20 are to be installed on a vertebral column 24, the spinous processes 36 are removed and the holes 40 are drilled in the vertebrae 22. Force transmitting members 44 are then mounted in the displaced vertebra 22a, the pair of vertebra 22 immediately above the displaced vertebra 22a, and the pair of vertebra 22 immediately below the displaced vertebra 22a. To mount a force transmitting member 44, it is pressed axially into a hole 40 formed in the vertebra 22 (see FIG. 7) and twisted by applying torque to the wrenching flats 70. This causes the helix 56 to twist into the hole 40.

When the force transmitting members 44 have been mounted in the vertebra 22, the force transmitting members extend outwardly from the vertebra in a vertical array. A spinal plate 30 is then positioned on the vertebral column with the force transitting members 44 extending through slots 52 formed along the longitudinal central axis of the spinal plate 30 (see FIG. 9). The force transmitting member 30 is then pressed into firm abutting engagement with the vertebrae 22 immediately above and below the displaced vertebra 22a by tightening the nuts 50 on the outwardly projecting retaining end portions 48 of the force transmitting members 44. This results in the spinal plate 30 being firmly anchored in a position in which it bridges the space across the displaced vertebra 22a.

Positioning of the spinal plate 30 is facilitated because the axially extending slots 52 in the spinal plate enables its position to be adjusted to accommodate different size vertebrae 22. Thus, the axial position of the spinal plate 30 can be adjusted vertically relative to the vertebrae 22. If a single circular hole had been provided in the spinal plate 30 for each of the force transmitting members 44, the force transmitting members 44 would have to be located relative to the vertebrae in positions dictated by the locations of the holes in the spinal plate rather than by the size and shape of the vertebrae forming the spinal column.

Once the spinal plate 30 has been firmly anchored by the fastener assemblies 32 disposed on opposite sides of the displaced vertebra 22a, the fastener assembly 32 connected with the displaced vertebra 22a is tightened. This causes the displaced vertebra to be pulled to the desired position under the influence of axial forces applied to the displaced vertebra by the force transmitting member 44.

To tighten the fastener assembly 32, the nut 50 is rotated relative to the external threads 74 on the retaining end portion 48 of the force transmitting member. As the nut 50 is rotated, the wrenching flats 70 (see FIG. 6) are held to prevent the application of twisting or torsional forces to the vertebra 22a. This results in the vertebra 22a being pulled straight rightwardly from the displaced position shown in solid lines in FIG. 8 to the desired position shown in dashed lines. Due to the absence of torsional or twisting forces on the vertebra 22a, the vertebra does not tend to become twisted or cocked relative to the adjacent vertebra 22b and 22c. When the fasteners 32 have been tightened and the displaced vertebra 22a moved to the desired position, the projecting end portions of the force transmitting members 44 are cut off.

Figure 8:
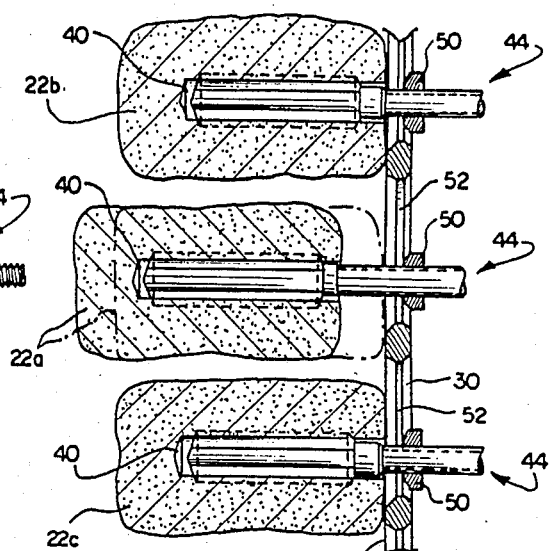
FIG. 8 is a schematic illustration depicting the manner in which the displaced vertebra is moved relative to the adjacent vertebra to reduce the displacement between the vertebrae.

In the specific instance illustrated in FIG. 8, the displaced vertebra 22a is pulled into abutting engagement with the spinal plate 30 by tightening the nut 50 on the force transmitting member 44. However, it is contemplated that in certain circumstances it may be desirable to pull the displaced vertebra 22a only part way toward the spinal plate 30 so that there is a small space between the spinal plate and the previously displaced vertebra 22a. In addtion, it is contemplated that the spinal plate 30 may cooperate with the vertebra 22b or the vertebra 22c to move either or both of these vertebrae from a displaced position to a desired position along with the vertebra 22a.

Spinal Plate

The construction of the spinal plate 30 is illustrated in FIGS. 9-11. The spinal plate 30 includes a pair of parallel longitudinally extending beam sections 88 and 90 which are interconnected by a plurality of cross sections 94, 96, 98, 100, 102 and 104. The cross sections 94-104 cooperate with the beam sections 88 and 90 to define the slots 52.

The spinal plate 30 has a bottom side surface 108 (FIG. 11) in which a plurality of grooves 110 are formed. The grooves 110 tend to prevent sliding of the spinal plate 30 relative to the vertebrae 22. In addition, the bony material of the vertebrae 22 tends to grow into the grooves 110 to further hold the spine plate 30 against movement relative to the vertebrae 22.

The slots 52 are provided with a bevelled upper or outer edge portions 114 (FIG. 9) which slopes at the same angle as the conical outer side surface 82 (see FIG. 6) of the nut 50. A plurality of scallops or recesses 116 are provided in the bevelled edge portions 114 to engage conical side surfaces 82 of the nut 50. The recesses 116 hold the nuts 50 against sidewise movement relative to the spinal plate 30. The recesses 116 are defined by surfaces which form a portion of a cone having the same included angle as the side surfaces 82 of the nuts 50.

Fastener Assembly—Second Embodiment

In the embodiment of the invention illustrated in FIGS. 1-11, the fastener assemblies 32 are provided with force transmitting members 44 having helices 56 which engage the bony material of the vertebrae 22. In the embodiment of the invention illustrated in FIGS. 12-14, the fastener assemblies are provided with inserts which re engaged by the force transmitting members and are expanded into gripping engagement with the underside surfaces of the holes formed in the vertebrae. Since the embodiment of the invention illustrated in FIGS. 12-14 is generally similar to the embodiment of the invention illustrated in FIGS. 1-11, similar numerals will be utilized to designate similar components.

Figure 12:
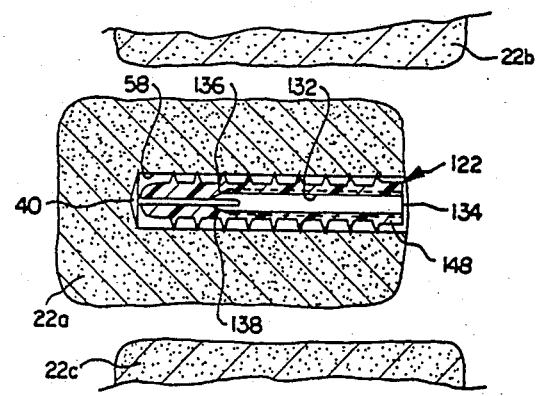
FIG. 12 is a schematic illustration of a second embodiment of the invention in which an insert is mounted in an opening formed in a vertebra.
Figure 13:
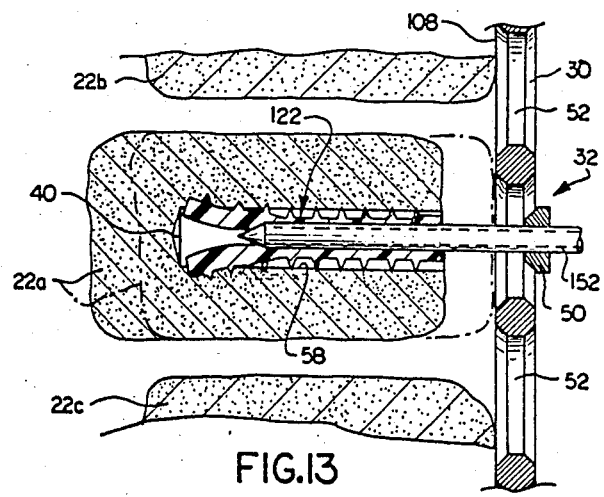
FIG. 13 is a fragmentary schematic illustration, generally similar to FIG. 8, illustrating the manner in which the extent of displacement between adjacent vertebrae is reduced with the second embodiment of the invention.
Figure 14:
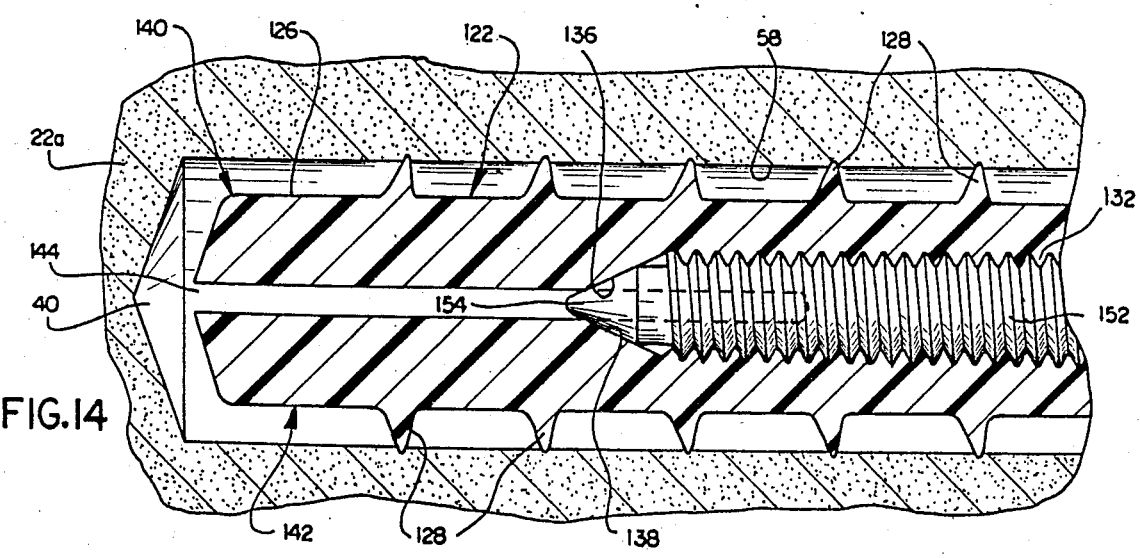
FIG. 14 is an enlarged fragmentary sectional view illustrating the relationship between the insert of FIG. 12 and a force transmitting member, the insert being shown in a contracted position prior to being expanded into engagement with the side of a hole formed in a vertebra.

In the embodiment of the invention shown in FIGS. 12-14, each of the fastener assemblies 32 includes an insert 122 which is actuated from the contracted condition of FIGS. 12 and 14 to the expanded condition of FIG. 13 to firmly grip the inner side surface 58 of a hole 40 formed in the vertebra 22a. The insert 122 is molded of one piece from a suitable polymeric material, such as polyethylene.

The insert 122 has a cylindrical outer side wall 126 (FIG. 14) from which a plurality of annular ridges 128 extend. The insert 122 has a threaded central opening 132. The opening 132 extends inwardly from an end surface 134 (FIG. 12) to cam surfaces 136 and 138 formed on end sections 140 and 142 of the insert. The end sections 140 and 142 are separated by an axially extending slot 144 which extends diametrically across one end of the insert 122.

The insert 122 is positioned in the hole 40 by forcing the insert axially into the hole while rotating the insert about its central axis. To facilitate insertion of the insert 122 into the hole 40, the insert is provided with wrenching flats 148 at the outer end of the fastener.

Once the insert 122 has been positioned in the hole 40, an externally threaded force transmitting member 152 is turned into the internally threaded central opening 132 in the insert. As the force transmitting member 152 moves into the insert, a leading conical end portion 154 of the force transmitting member 152 moves into abutting engagement with the cam surfaces 136 and 138. Continued rotation of the force transmitting member 152 causes the conical leading end portion 154 of the force transmitting member 152 to separate or cam the end sections 140 and 142 apart to expand the fastener (see FIG. 13).

As the end sections 140 and 142 are separated by the camming action of the force transmitting member 152 against the cam surfaces 136 and 138, the annular ridges 128 on the end sections 140 and 142 are pressed into the bony material of the vertebra 22. The outer end of the force transmitting member 152 may be provided with wrenching flats to facilitate rotation of the force transmitting member 152 relative to the insert 122.

After the insert 122 has been expanded by the force transmitting member 152, a nut 50 (see FIG. 13) is turned onto the force transmitting member 152. The ridges 128 hold the insert 122 against rotation relative to the vertebra 22a as the nut 50 is rotated. As the nut 50 is rotated, the force transmitting member 152 pulls the vertebra 22a from the displaced position shown in solid lines in FIG. 13 to a desired position shown in dashed lines in FIG. 13.

Summary

The present invention provides an apparatus 20 which reduces the extent of displacement between adjacent vertebrae 22 by pulling a displaced vertebra 22a into a desired position (shown in dashed line in FIG. 8) and maintaining it in the desired position. When the apparatus is to be installed on the spinal column 24 of a person, a force transmitting member 44 is mounted in an opening 40 formed in the displaced vertebra 22a. A spinal plate 30 is then positioned so that it extends across the displaced vertebra 22a into abutting engagement with vertebrae 22b and 22c on opposite sides of the displaced vertebra. The displaced vertebra 22a is then pulled into the desired relationship with te adjacent vertebrae by tightening a nut 50 on an outwardly projecting end portion of the force transmitting member 44. Since the force transmitting member 44 was previously connected with the displaced vertebra 22a, tightening of the nut 50 applies little or no torsional froce to the displaced vertebra 22a. Therefore, tightening the nut 50 pulls the displaced vertebra 22a straight outward from the displaced position shown in solid lines in FIG. 8 toward the desired position shown in dashed lines in FIG. 8 with a minimum of twisting of the displaced vertebra 22a.

Having described specific preferred embodiments of the invention, the following is claimed:

1. An apparatus for use with fasteners for maintaining vertebrae in a desired relationship, said apparatus comprising:

an elongated plate for connecting at least two vertebrae, said elongated plate having a first major side surface for facing the vertebrae and a second major side surface extending generally parallel to said first major side surface, said first and second major side surfaces having first and second minor side surfaces extending therebetween;

said elongated plate also having at least one elongated slot extending therethrough and intersecting said first and second major side surfaces and located along the longitudinal central axis of said elongated plate, said slot being capable of receiving a fastener therein at any one of a plurality of locations along the slot and which fastener is connectable with a vertebra; and said slot being defined by opposed slot surfaces extending longitudinally of said elongated plate and arcuate recesses in said opposed slot surfaces and spaced therealong, the recesses in one of said opposed slot surfaces being aligned with the recesses in the other of said opposed slot surfaces to define said plurality of locations, said recesses comprising means for blocking sliding movement of aid elongated plate relative to the fastener and of said elongated plate relative to the vertebrae when the fastener is located in a pair of aligned recesses.

2. An apparatus as set forth in claim 1 wherein each of said recesses has a frustoconical configuration for engaging an exterior surface of the fastener to center the fastener relative to said recess.

3. An apparatus as defined in claim 1 wherein each of said recesses is defined by a frustoconical surface which extends between said second major side surface and one of said opposed slot surfaces defining said slot, said elongated plate being of sufficient length to span at least three adjacent vertebrae and including a plurality of slots located along the longitudinal central axis of said elongated plate, and each of said plurality of slots being disposed along said elongated plate to receive a fastener connectable with a vertebra therethrough.

4. An apparatus for maintaining vertebrae in a desired relationship, said apparatus comprising:

an elongated plate for connecting at least two vertebrae, said elongated plate having a first major side surface for facing the vertebrae and a second major side surface extending generally parallel to said first major side surface, said first and second major side surfaces having first and second minor side surfaces extending therebetween;

a pair of fasteners for connecting said elongated plate to the vertebrae, each of said pair of fasteners for connecting said elongated plate to a respective one of the vertebrae;

said elongated plate also having at least one elongated slot extending therethrough and intersecting said first and second major side surfaces and located along the longitudinal central axis of said elongated plate, said slot being capable of receiving at least one of said fasteners therein at any one of a plurality of locations along the slot; and said slot being defiend by opposed slot surfaces extending longitudinally of said elongated plate and arcuate recesses in said opposed slot surfaces and spaced therealong, the recesses in one of said opposed slot surfaces being alinged with the recesses in the other of said opposed slot surfaces to defined said plurality of locations, said recesses comprising means for blocking sliding movement of said elongated plate relative to said fasteners and sliding movement of said elongated plate relative to the vertebrae when a fastener engages a recess.

5. An apparatus as set forth in claim 4 wherein each of said recesses has a frustoconical configuration for engaging an exterior surface of said fasteners to center each fastener relative to said recess.

6. An apparatus as defined in claim 4 wherein each of said recesses is defined by a frustoconical surface which extends between said second major side surface and one of said opposed slot surfaces defining said slot, said elongated plate being of sufficient length to span at least three adjacent vertebrae and including a plurality of slots located along the longitudinal central axis of said elongated plate, and each of said plurality of slots being disposed along said elongated plate to receive one of said fasteners connectable with a vertebra therethrough.

7. An apparatus comprising:

an elongated plate for connecting at least two vertebrae, said elongated plate having a first major side surface for facing the vertebrae and a second major side surface extending generally parallel to said first major side surface, said first and second major side surfaces having first and second minor side surfaces extending therebetween;

said elongated plate also having at least one elongated slot extending therethrough and intersecting said first and second major side surfaces, said elongated slot being located along the longitudinal central axis of said elongated plate; and said slot being defined by opposed slot surfaces extending longitudinally of said elongated plate and arcuate surfaces forming recesses in said opposed slot surface and spaced therealong, the arcuate surface in one of said opposed slot surfaces being aligned with the arcuate surfaces in the other of said parallel surfaces to define a fastener seat, said fastener seat comprising means for blocking sliding movement of said elongated plate relative to a fastener and of said elongated plate relative to a vertebra when the fastener is located in a fastener seat and clamps the elongated plate to the vertebrae.

8. An apparatus as defined in claim 1 wherein said opposed slot surfaces are substantially perpendicular to said second major side surface.

* * * * *